US00PP34131P2

(12) United States Plant Patent
Hansen

(10) Patent No.: US PP34,131 P2
(45) Date of Patent: Apr. 12, 2022

(54) ***MONARDA* PLANT NAMED 'PARDON MY LAVENDER II'**

(50) Latin Name: *Monarda didyma*
Varietal Denomination: Pardon My Lavendar II

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 17/300,859

(22) Filed: Nov. 29, 2021

(51) Int. Cl.
*A01H 5/02* (2018.01)
*A01H 6/50* (2018.01)

(52) U.S. Cl.
USPC ..... Plt./455
CPC ..... *A01H 6/50* (2018.05)

(58) Field of Classification Search
USPC ..... Plt./455
CPC ..... A01H 5/02
See application file for complete search history.

*Primary Examiner* — Kent L Bell

(57) ABSTRACT

The new and distinct cultivar of ornamental cultivar of bee balm plant named *Monarda didyma* 'Pardon My Lavender II' has short, compact, basally branching stems, medium to dark green foliage with numerous large, lavender-pink colored flowers creating excellent flower coverage and strong foliar resistance to powdery mildew.

1 Drawing Sheet

Botanical classification: *Monarda didyma.*
Variety denomination: 'Pardon My Lavender II'.

STATEMENT REGARDING PRIOR DISCLOSURES UNDER 37 CFR 1.77(B)(6)

The first public disclosure of the claimed plant, in the form of a sale, was made by Walters Gardens, Inc. on Jul. 7, 2021. Prior to that, on Dec. 1, 2020 the claimed plant was displayed with a non-enabling photograph and brief description in a website operated by Walters Gardens, Inc., and on May 21, 2021 as a non-enabling photograph and brief description in the 2021-2022 Catalog by Walters Gardens, Inc., who obtained the plant and all information relating thereto, from the inventor. No plants of *Monarda* 'Pardon My Lavender II' have been sold, in this country or anywhere in the world, nor has any disclosure of the new plant been made more than one year prior the filing date of this application, and such sale or disclosure within one year was either derived directly or indirectly from the inventor.

BACKGROUND OF THE INVENTION

The present invention relates to the new and distinct cultivar of bee balm plant, botanically known as *Monarda didyma* 'Pardon My Lavender II', and hereinafter also referred to solely as the cultivar 'Pardon My Lavender II' or the "new plant". The new plant was selected from seed collected by the hybridizer from a self-pollination on Jun. 17, 2015 at a nursery in Zeeland, Mich., USA of a proprietary unreleased hybrid known only as 14-57-3 not patented. The plant was a single selection originally made in the summer of 2017 from the seeds that were sown in the fall of 2015, and the new plant was assigned the temporary breeder code of 15-54-5.

The new plant has been asexually propagated by division followed by basal shoot tip cuttings originally in 2017 at the same nursery in the greenhouses in Zeeland, Mich., and the subsequent asexually propagated plants found to be stable, true to type and identical to the original selection.

BRIEF SUMMARY OF THE PLANT

*Monarda didyma* 'Pardon My Lavender II' is unique from its parents and all other bee balm plants known to the inventors. The nearest comparison varieties are: 'Pardon My Lavender' U.S. Plant Pat. No. 28,770, 'Leading Lady Orchid' U.S. Plant Pat. No. 33,132, 'Leading Lady Plum' U.S. Plant Pat. No. 26,447, 'Lilac Lollipop' U.S. Plant Pat. No. 27,571 'Pardon My Purple' U.S. Plant Pat. No. 22,170 and 'Purple Lace' U.S. Plant Pat. No. 25,615.

'Pardon My Lavender' has a lighter lavender-pink flower without the anthocyanin on the bracts and foliage. 'Leading Lady Orchid' and 'Leading Lady Plum' have taller habits, the former with orchid-pink flowers and the latter with deeper magenta-pink flowers, both with darker spotting on the lower petal. 'Lilac Lollipop' has a slightly taller and narrower habit with less vigor and the flower is lavender-lilac. 'Pardon My Purple' has flowers of deeper fuchsia-purple. 'Purple Lace' has a deeper reddish-purple flower.

Comparison with the parent 14-57-3 has a taller habit with lighter-colored flowers that do not cover the plant as completely.

The following are traits of *Monarda didyma* 'Pardon My Lavender II' that in combination distinguish it from all other bee balm known to the inventor:

1. Short, winter-hardy, compact, vigorous, clumping habit;
2. Medium to dark-green leaves with good resistance to powdery mildew;
3. Large-sized heads of lavender-pink colored flowers for a long period in summer with excellent flower coverage;
4. Flower heads subtended by burgundy-colored bracts.

BRIEF DESCRIPTION OF THE DRAWINGS

The photographs of the new plant demonstrate the unique traits of 'Pardon My Lavender II' and the overall appearance of the plant at two-years old in the full sun trial garden of a nursery in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
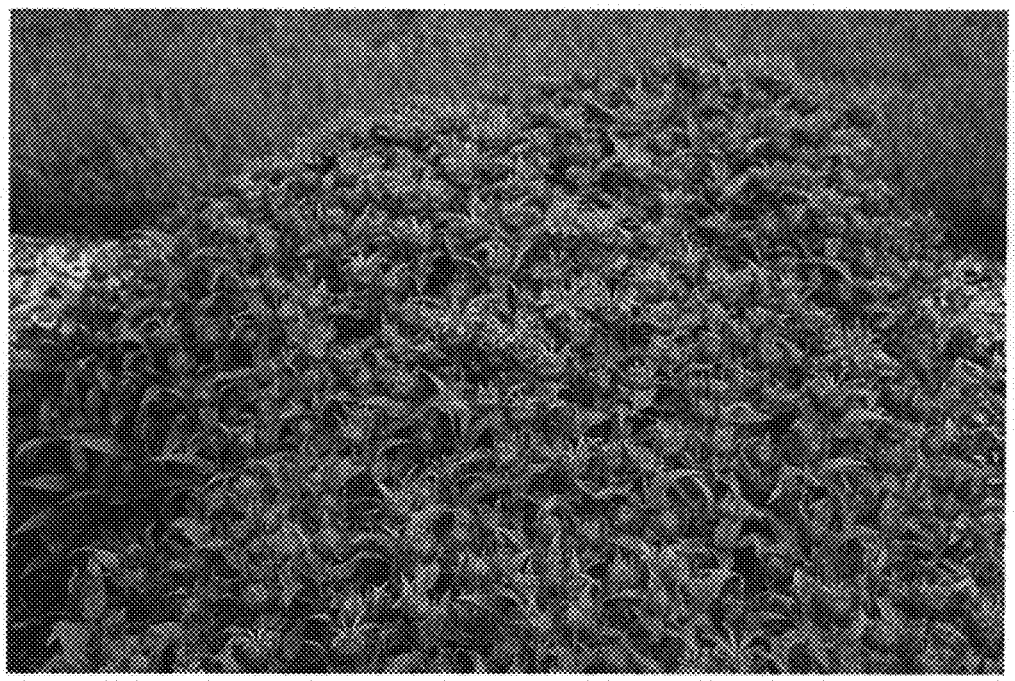
FIG. 1 shows the new plant in flower in the landscape in early flowering stage.
Figure 2:
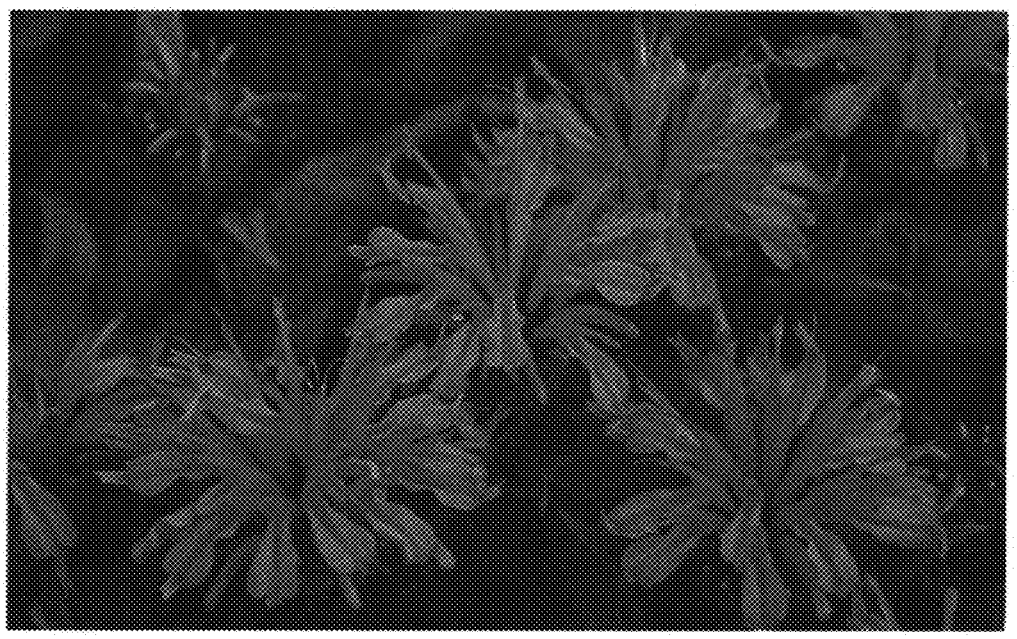
FIG. 2 shows a close-up of the flowers with buds and burgundy bracts.

The following descriptions and color references are based on the 2015 edition of The Royal Horticultural Society Colour Chart except where common dictionary terms are used. *Monarda* 'Pardon My Lavender II' has not been observed under all possible environments. The phenotype may vary slightly with different growing environments such as temperature, light, fertility, soil pH, moisture and maturity levels, but without any change in the genotype. The following observations and size descriptions are based on two-year-old plants grown in a trial garden at a nursery in Zeeland, Mich. with supplemental fertilizer and water as needed.

Botanical classification: *Monarda* hybrid;

Parentage: The female (seed) parent is 15-54-3, an unreleased proprietary hybrid; the male (pollen) parent is also 15-54-3;

Plant habit: Hardy herbaceous perennial, dense, upright mound, producing multiple stems spreading by short rhizomes near the base of the stems; foliage up to 41.0 cm tall, flowering to 45.0 cm tall and 70.0 cm wide; flowering begins late spring in Michigan and continuing for about 5 weeks;

Propagation: Stem cuttings;

Time to produce finished crop in 3.8-liter pots: About 7 to 9 weeks; moderate rate of growth;

Root: Fine, fibrous and freely branching; color creamy white to tan depending on soil type;

Leaves: Simple; lanceolate; opposite; margin serrated and ciliolate; puberulent above and below; moderately lustrous adaxial, matte to slightly lustrous abaxial; narrowly acute apex; cordate to rounded base; to about 7.0 cm long and 4.0 cm wide, average about 6.0 cm long and 3.3 cm wide near base;

Leaf color: Young expanding leaves adaxial between RHS 138B and RHS 145A with a moderate blush of nearest RHS 187A along margin, abaxial nearest RHS 146B with light to moderate blush of nearest RHS 187A; mature leaves adaxial between RHS 137A and RHS 136A with portions high in anthocyanins nearest RHS N186C, abaxial nearest RHS 147B with portions high in anthocyanins nearest RHS 187B;

Foliage fragrance: Pleasant lemony-herbal;

Veins: Pinnate; glabrous and slightly sunken adaxial, abaxial puberulent and costate with pubescent midrib;

Vein color: Adaxial midrib variable, nearest RHS N186C and nearest RHS 147C, lateral pinnate veins and secondary veins between RHS 137A and RHS 138A; abaxial midrib variable, between RHS 146B and RHS 146C with frequent moderate to weak anthocyanin blush of nearest RHS 187B and with lateral pinnate veins region nearest RHS 147C, secondary veins nearest RHS 146B and distal pinnate and secondary veins nearest RHS 187B;

Petiole: Micro-puberulent, slightly concaved above; to about 4.0 mm long and 2.0 mm across at base;

Petiole color: Adaxial nearest RHS N186C and abaxial nearest RHS 146D with a slight to strong blush of nearest RHS N186C;

Stems: Quadrangular; pubescent to puberulent; about 0.5 cm across at base and 41 cm long; about 80 per plant; naturally branched at upper nodes; 16 to 20 nodes per stem; average 2.0 cm between nodes greater distally;

Stem color: Nearest RHS 146B with heavy anthocyanin expression in high light nearest RHS 187A to nearly solid RHS 187A in distal region; nodes same color as surrounding stem;

Flowers: Single, bilabiate flowers arranged in mostly terminal verticils forming globular head about 78.0 mm across and 37.0 mm tall, opening from the center and progressing outwardly and down; attitude outwardly to upwardly; individual flowers to about 38.0 mm long to exserted stigma, 17.0 mm tall and about 7.0 mm across; individual flowers persisting about 5 days in Michigan; numerous, about 150 to 200 flowers per terminal head, fewer per axillary head; 150 inflorescences with open flowers at one time in peak flower;

Flower fragrance: Sweet lemony;

Buds one to two days prior to opening: Narrowly oblanceolate, arcuate downward; about 25.0 mm long and 3.0 mm across and 12.0 mm tall;

Bud color: Basal 4.0 mm nearest RHS 155D, distal and dorsal portion nearest RHS 61C, ventral region nearest RHS 62D;

Petals: Bilabiate; arcuate downward; basal 23.0 mm fused into tube; split in two in the distal 17.0 mm, corolla to about 33.0 mm long; abaxial glandular to puberulent, adaxial glabrous outside of corolla tube, micro-puberulent adaxial corolla tube; self-cleaning;

Upper labium: Rolled or folded in middle portion, about 12.0 mm long from fusion to rounded and slightly reflexed apex, 5.0 mm tall, 2.5 mm across at base, about 4.0 mm across in middle when flattened;

Lower labium: About 16.0 mm long from fusion to apex, apex comprising three lobes including two side lobes about 1.0 mm long and 2.0 mm across with rounded apex, center lobe about 6.0 mm long and 2.0 mm across with sharply-acute emarginate apex in the distal 1.0 mm;

Petal color: Upper labium adaxial surface proximally between RHS 72B and RHS 72C, upper labium abaxial surface between RHS 72A and RHS N78A; lower labium adaxial and abaxial surfaces between RHS 72C and RHS 70B with emarginate apex nearest RHS N82C; corolla tube abaxial proximal 5.0 mm nearest RHS NN155C, and distally nearest RHS NN155B, adaxial tube basal 5.0 mm nearest RHS NN155B and distally nearest RHS 84C;

Androecium: Two; adnate inner corolla tube in basal portion;

*Filaments*.—Two; curved downward; adnate the inner corolla tube in the basal 20.0 mm and free in the distal 11.0 mm; about 0.5 mm diameter; distal color nearest RHS 75D, proximal color basal 5.0 mm nearest RHS NN155B and middle nearest RHS 85D.

*Anther*.—Two, fused longitudinally; oblong elliptic, dorsifixed, longitudinal; 2.5 mm long by 1.0 mm wide; dorsal color between RHS 83B and RHS N79D and ventral suture color nearest RHS 79A.

*Pollen*.—Abundant, elliptic to globose, less than 0.1 mm; color between RHS16D and RHS 16CB.

Gynoecium: Single; superior; about 41.0 mm long;

Pistil: One per flower; protruding about 6.0 mm beyond upper labium when mature;

Style: Cylindrical; glabrous; about 38.0 mm long and about 0.5 mm diameter; slightly arcuate along upper labium; color nearest RHS N81C in distal 5.0 mm transitioning to nearest RHS NN155D in middle and basal portion;

Stigma: Unevenly bifid in the distal 2.0 mm with one portion 1.0 mm and the other 2.0 mm long, about 0.2 mm in diameter; color nearest RHS N82B;

Ovary: Conical; about 1.0 mm tall by 0.75 mm diameter; color nearest RHS 145D;

Calyx: Tubular; consisting of five fused sepals; about 12.0 mm long and 3.0 mm diameter at apex;

Sepals: Five; acute apex; basal 10.5 mm fused forming calyx tube, free in distal 1.5 mm; margin micro-ciliolate; about 12.0 mm long and 1.0 mm across at fusion; micro-puberulent abaxial, glabrous adaxial except throat pubescent; persistent;

Sepal color: Adaxial and abaxial basal 2.0 mm nearest RHS 145D, middle adaxial portion nearest RHS 145C with veins nearest RHS 138B, middle abaxial potion between RHS 146D and RHS 145D with veins moderately blushed with anthocyanin nearest RHS 187B, distal 1.0 mm adaxial portion nearest RHS 187A and distal 2.0 mm abaxial portion nearest RHS 187A;

Foliar bracts: Typically one set of five to seven large bracts on the outside per inflorescence and one set of six smaller bracts in the middle and one set of about 24 to 30 smaller narrow bracts on the inside below each inflorescence; outer bracts lanceolate with acute apex and attenuate sessile base, micro-ciliolate margin, glabrous adaxial, puberulent abaxial, flat to coarsely wavy, slightly lustrous adaxial and matte abaxial, to 30.0 mm long and 15.0 mm wide in center, decreasing in size toward flowers; innermost bracts linear, narrowly acute apex and truncate base, ciliolate margin, adaxial and abaxial glabrous, to about 12.0 mm long and 1.5 mm across at base, Foliar bract color: Variable; adaxial with heavy anthocyanin between RHS 187B and RHS N186C or distally nearest RHS 137C and proximally nearest RHS 145A, midrib nearest RHS N77D or RHS 187C; color abaxial nearest RHS 146B with midrib nearest RHS 145C; innermost bracts color variable, distally adaxial and abaxial nearest RHS 187B and proximally adaxial and abaxial transitioning to between RHS 146D and RHS 145D at base;

Peduncle: Pubescent, stiff, strong, erect, quadrangular; to about 3.0 mm across and average 45.0 mm long above node last node; about 150 per plant; naturally branched at nodes;

Peduncle color: Variable between RHS 146C and RHS 144A with squared corners heavily blushed with nearest 187A;

Pedicel: About 2.0 mm long and 0.8 mm diameter; color nearest RHS 145B;

Fruit: Single, glabrous, lustrous, ellipsoidal nutlet; about 1.2 mm long and 0.7 mm wide; color nearest RHS 200C;

Hardiness: The new plant grows best with plenty of moisture and adequate drainage; hardy to at least from USDA zone 4 through 8.

Disease and pest resistance: Demonstrated greater than average powdery mildew tolerance in side-by-side comparison with other *Monarda*.

I claim:

1. A new and distinct cultivar of ornamental Bee Balm plant named *Monarda* 'Pardon My Lavender II', as herein described and illustrated.

* * * * *